(12) United States Patent
Single (10) Patent No.: US 11,672,976 B2
(45) Date of Patent: Jun. 13, 2023

(54) LEAD FOR AN ACTIVE IMPLANTABLE MEDICAL DEVICE WITH DECOY

(71) Applicant: Saluda Medical Pty Limited, Artarmon (AU)

(72) Inventor: Peter Scott Vallack Single, Artarmon (AU)

(73) Assignee: Saluda Medical Pty Limited, Artarmon (AU)

( * ) Notice: Subject to any disclaimer, the term of this patent is extended or adjusted under 35 U.S.C. 154(b) by 44 days.

(21) Appl. No.: 17/065,687

(22) Filed: Oct. 8, 2020

(65) Prior Publication Data

US 2021/0106818 A1 Apr. 15, 2021

(30) Foreign Application Priority Data

Oct. 10, 2019 (AU) .................................. 2019903815

(51) Int. Cl.
*A61N 1/36* (2006.01)
*A61N 1/08* (2006.01)
*A61N 1/05* (2006.01)

(52) U.S. Cl.
CPC ........... *A61N 1/086* (2017.08); *A61N 1/3605* (2013.01); *A61N 1/0534* (2013.01); *A61N 1/0551* (2013.01)

(58) Field of Classification Search
CPC .... A61N 1/086; A61N 1/3605; A61N 1/0534; A61N 1/0551
See application file for complete search history.

(56) References Cited

U.S. PATENT DOCUMENTS

| 7,174,219 | B2 | 2/2007 | Wahlstrand et al. | |
| 7,844,344 | B2 | 11/2010 | Wahlstrand et al. | |
| 7,853,332 | B2 | 12/2010 | Olsen et al. | |
| 7,877,150 | B2 | 1/2011 | Hoegh et al. | |
| 8,275,464 | B2 * | 9/2012 | Li ........................ | A61N 1/3718 607/116 |
| 8,620,453 | B2 | 12/2013 | Wahlstrand et al. | |

(Continued)

FOREIGN PATENT DOCUMENTS

WO 2017086805 5/2017

OTHER PUBLICATIONS

Hartung et al., "MRI Safe Electrodes for Spinal Cord Stimulation (SCS)", Presented at the 13th World Congress of the International Neuromodulation Society, Edinburgh, Scotland, May 27-Jun. 1, 2017, 3 pages.

(Continued)

*Primary Examiner* — Ankit D Tejani
*Assistant Examiner* — Joshua Brendon Solomon
(74) *Attorney, Agent, or Firm* — KPPB LLP (57) ABSTRACT

A lead (1) for an active implantable medical device comprising: an elongated, biocompatible, electrically non-conductive body (3); a plurality of electrically conductive filaments (5) inside the elongated body (3) to electrically connect electrical connectors (6) to corresponding electrodes (8); and at least one elongated decoy conductor (10) inside the elongated body (3) to electromagnetically couple with the plurality of electrically conductive filaments (5), wherein the at least one decoy conductor (10) has a higher electrical resistance than the plurality of electrical conductive filaments (5) to dissipate energy from currents induced by radio frequencies.

17 Claims, 5 Drawing Sheets

(56) References Cited

U.S. PATENT DOCUMENTS

| | | |
|---|---|---|
| 8,798,767 B2 | 8/2014 | Foster et al. |
| 8,989,840 B2 | 3/2015 | Przybyszewski et al. |
| 9,050,457 B2 | 6/2015 | Foster et al. |
| 11,077,296 B2 | 8/2021 | Mccabe et al. |
| 2009/0171421 A1* | 7/2009 | Atalar .................... A61N 1/056 607/63 |
| 2011/0066196 A1* | 3/2011 | Alexander ........... A61N 1/0551 607/116 |
| 2013/0150938 A1* | 6/2013 | Carbunaru ........... A61N 1/0551 607/116 |
| 2014/0031907 A1* | 1/2014 | Williams ............... A61N 1/056 607/116 |
| 2014/0052203 A1* | 2/2014 | Bulkes .................... A61N 1/05 607/9 |
| 2018/0229031 A1* | 8/2018 | Searfoss ............... A61L 31/024 |
| 2018/0326202 A1* | 11/2018 | McCabe ................. A61N 1/06 |

OTHER PUBLICATIONS

McCabe et al., "A Novel Implant Electrode Design Safe in the RF Field of MRI Scanners", Department of Engineering, The University of Waikato, Dec. 28, 2016, 7 pages.

McCabe et al., "New MRI-safe Implant Electrode Design", In 2016 IEEE MTT-S International Microwave Symposium (IMS), San Francisco, CA, 3 pgs., https://doi.org/10.1109/MWSYM.2016.7540205.

\* cited by examiner

LEAD FOR AN ACTIVE IMPLANTABLE MEDICAL DEVICE WITH DECOY

TECHNICAL FIELD

The present disclosure relates to lead for an active implantable medical device (AIMD) for implanting into tissue of a patient.

BACKGROUND

Medical devices having one or more active implantable components, generally referred to herein as active implantable medical devices (AIMDs), have provided a wide range of therapeutic benefits to patients over recent decades. AIMDs often include an implantable, hermetically sealed electronics module, and a device that interfaces with a patient's tissue, sometimes referred to as a tissue interface. The tissue interface may include, for example, one or more instruments, apparatus, sensors or other functional components that are permanently or temporarily implanted in a patient. The tissue interface is used to, for example, diagnose, monitor, and/or treat a disease or injury, or to modify a patient's anatomy or physiological process.

In particular applications, an AIMD tissue interface includes one or more conductive electrical contacts, referred to as electrodes, which deliver electrical stimulation signals to, or receive signals from, a patient's tissue. The electrodes are typically disposed in a biocompatible electrically non-conductive member, and are electrically connected to the electronics module. The electrodes and the non-conductive member are collectively referred to herein as an electrode assembly.

For neuro-stimulators, the tissue interface is a stimulating lead 1000 which delivers electrical pulse to a specific nerve or tissue. This lead 1000 may consist of a long thin non-conductive (and insulating) body 1004 and a number of conductive rings 1006, 1008 at both ends 1007, 1009 of the body 1004. Referring to FIGS. 4a, 4b, 5 and 6, the rings 1008 at a therapeutic end 1009 are known as electrodes and the rings 1006 at the connector end 1007 are known as contacts, where the electrodes are connected to the contacts along the long thin non-conductive body 1004. An example of the long thin non-conductive body 1004 is shown in the cross-section in FIG. 6 that shows conductive wires 1005 surrounded by a non-conductive body 1003. These conductive wires 1005 are sized to have lengths to conduct signals between corresponding conductive rings, such as the length of conductive wire 1005' that spans between 1006' and 1008' in FIGS. 4a and 4b. A different length of conductive wire 1005" spans between conductive rings 1006" and 1008".

Patients with an implanted neuro-stimulator and associated lead may have issues undergoing magnetic resonance imaging (MRI). The MRI uses three types of fields to create an image: a static magnetic field; a radiofrequency (RF) magnetic field; and a gradient magnetic field. Exposure to these fields may cause heating to the leads. This heating may result in tissue burns and damage (which may not be immediately felt by the patient). Another potentially damaging effect is damage to the implant due to radiofrequency energy being transmitted from the lead. This can lead to reprogramming, damage to the implant or explant of the implant. Additionally, the MRI could cause a temporary unintended stimulation due to induced voltage through the assembly and system.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

There have been attempts to provide designs for MRI safe leads. US patent publication U.S. Pat. No. 8,798,767 B2 illustrates a method of reducing the heat caused by MRI conditions. This document suggests coiling conductors in a multi-layer structure, with each coil layer electrically connected to the next to provide parallel conductive paths. However, this method may result in high inductance when exposed to MRI radiation. US patent publication U.S. Pat. No. 9,050,457 B2 uses a similar approach with a lead body and multi-layer coil conductor within the length of the lead body. The stiffness of the multi-layer coil conductor is similar to the lead body, ensuring consistent mechanical properties of the lead.

In light of the above mentioned issues, it would be advantageous to have an electrode assembly, such as one used in an implantable medical device, that may be implanted in a patient whilst the patient is undergoing magnetic resonance imaging. This may include providing an implantable electrode assembly which, when exposed to an MRI environment, does not generate significant heat in the leads due to electromagnetic currents. In may be further advantageous for an implantable medical device that can operate during magnetic resonance imaging without, or with reduced, side effects described above.

There is provided a lead for an active implantable medical device comprising: an elongated, biocompatible, electrically non-conductive body; a plurality of electrically conductive filaments inside the elongated body to electrically connect electrical connectors to corresponding electrodes; and at least one elongated decoy conductor inside the elongated body to electromagnetically couple with the plurality of electrically conductive filaments, wherein the at least one decoy conductor has a higher electrical resistance than the plurality of electrical conductive filaments to dissipate energy from currents induced by radio frequencies.

In some examples, the at least one elongated decoy conductor is located substantially parallel to the plurality of electrically conductive filaments.

In some examples, the at least one elongated decoy conductor is electrically insulated from the plurality of electrically conductive filaments, connectors and electrodes by the elongated body.

In some examples, the elongated body includes multiple lumens, wherein the multiple lumens receive one of the plurality of electrically conductive filaments or the at least one decoy conductor.

In further examples, the multiple lumens are arranged as a set of planetary lumens around a core of the elongated body.

In some examples, the multiple lumens include a dozen lumens.

In some examples, the at least one elongated conductor includes two or more elongated conductors evenly spaced from each other in the multiple lumens.

In some examples, the at least one elongated conductor includes four elongated conductors evenly spaced from each other in the multiple lumens.

In some examples, the at least one elongated decoy conductor is shorter than each of the plurality of electrically conductive filaments.

In some examples of the lead, a conductor length (L1) of the at least one elongated decoy conductor is approximately 90% of a length of the lead.

In some examples of the lead, a conductor length of the at least one elongated decoy conductor is matched with an expected wavelength of a radio frequency (RF) field from an MRI.

In some examples of the lead, a conductor length ($L_1$) of the at least one elongated decoy conductor is matched with an impedance equivalent to the characteristic impedance of the decoy filar.

In some examples of the lead, a conductor length (L1) includes odd integer multiples of half the expected wavelength of the RF field from the MRI. In some examples of MRI systems, the expected wavelengths include 64 MHz and/or 128 MHz.

In some examples of the lead, a conductor length ($L_1$) of the at least one elongated decoy conductor is in the range of 500 mm to 900 mm.

In some examples of the lead, the conductor length ($L_1$) of the at least one elongated decoy conductor is in the range of 10% to 90% of the length of the longest electrically conductive filament.

In some examples of the lead, the at least one elongated decoy conductor has a length specific resistance of 300 to 1000 Ohms/metre. In some examples, the decoy conductors have a resistivity that can enhance the electromagnetic coupling with the electrically conductive filaments.

In some examples of the lead, the at least one elongated decoy conductor comprises: nichrome and/or carbon fibre.

In some examples of the lead, each of the at least one elongated decoy conductors has a diameter of 70 μm to 200 μm.

In some examples of the lead, the elongated, biocompatible, electrically non-conductive body comprises thermoplastic polyurethane.

BRIEF DESCRIPTION OF DRAWINGS

FIGS. 3a and 3b illustrates yet another example of a lead for an active implantable medical device where

DESCRIPTION OF EMBODIMENTS

Aspects of the present disclosure are generally directed to an electrode assembly for an active implantable medical device (AIMD). An AIMD may include an implantable electronics module and a tissue interface. The electrode assembly that, at least in part, forms the tissue interface.

The electrode assembly may be used with one type of AIMD, a neuro stimulator, and more specifically a deep brain stimulator or spinal cord stimulator. Deep brain stimulators are a particular type of AIMD that deliver electrical stimulation to a patient's brain, while spinal cord stimulators deliver electrical stimulation to a patient's spinal column. As used herein, deep brain stimulators and spinal cord stimulators refer to devices that deliver electrical stimulation alone or in combination with other types of stimulation. It should be appreciated that embodiments of the present disclosure may be implemented in any brain stimulator (deep brain stimulators, cortical stimulators, etc.), spinal cord stimulator or other neuro stimulator now known or later developed, such as cardiac pacemakers/defibrillators, functional electrical stimulators (FES), pain stimulators, etc. Embodiments of the present disclosure may also be implemented in AIMDs that are implanted for a relatively short period of time to address acute conditions, as well in AIMDs that are implanted for a relatively long period of time to address chronic conditions.

The electrode assembly in accordance with embodiments of the present disclosure are not limited to devices that deliver electrical stimulation signals to a patient. For instance, in certain embodiments, the electrode assembly may be used to receive, record or monitor the physiological response of a patient's tissue to, for example, a therapy. In such embodiments, the electrodes receive a signal from the patient's tissue representing the physiological response. An electrode assembly of the present disclosure that delivers electrical stimulation signals to, or receives signals from, a patient's tissue may also include one or more other components, such as therapeutic agent delivery systems, sensors, etc., that interface with the patient's tissue.

Overview

Figure 1:
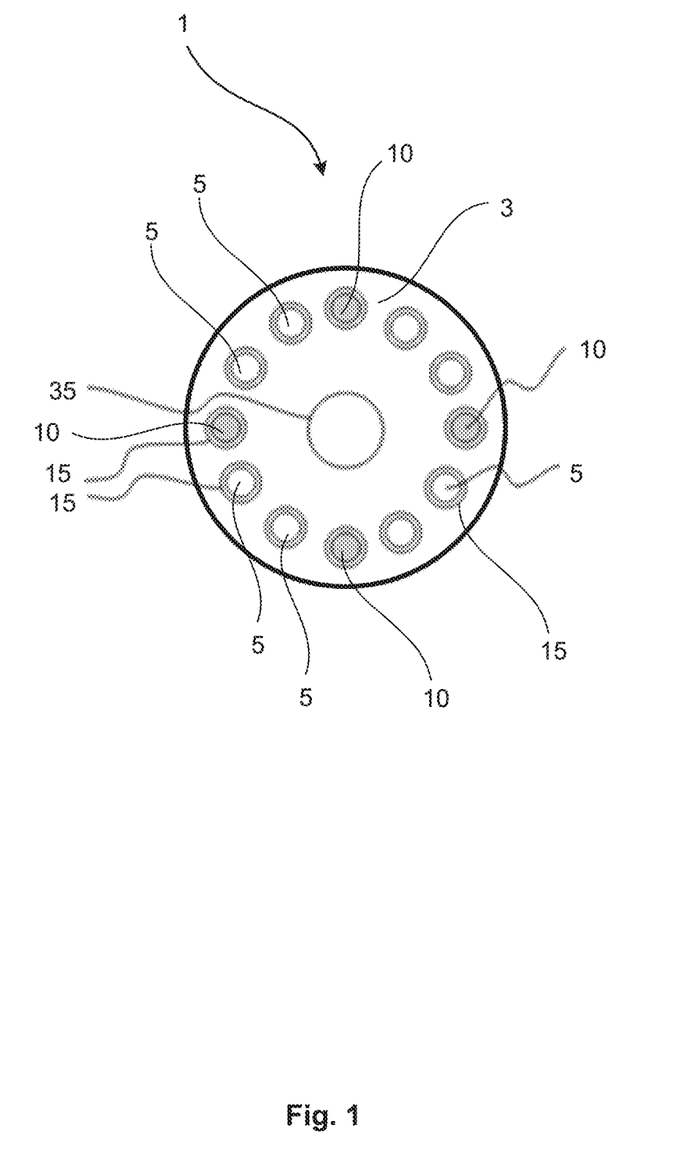
FIG. 1 illustrate a cross-section of a lead for an active implantable medical device with a decoy.
Figure 2:
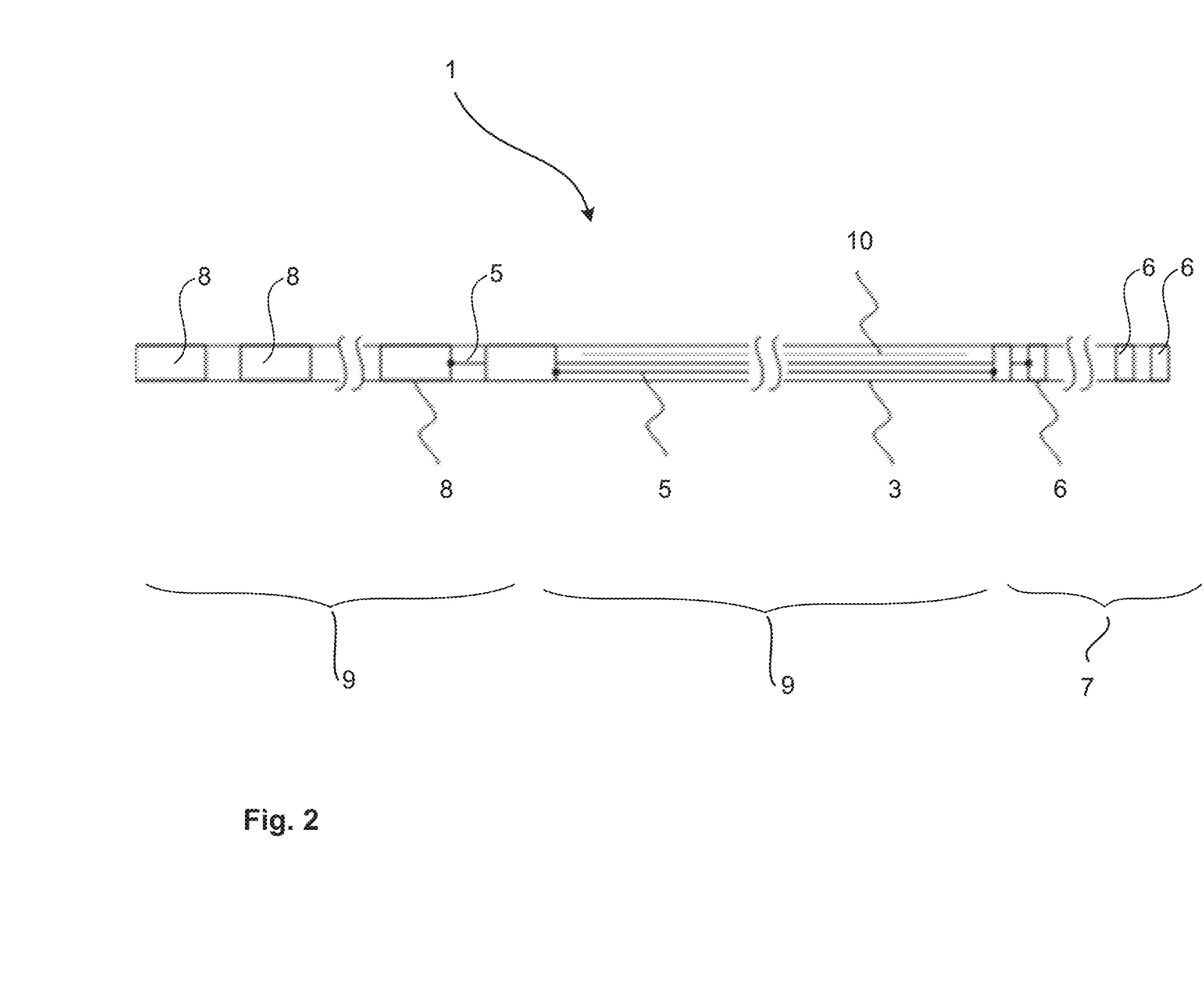
FIG. 2 is a schematic side view of the lead with a decoy of FIG. 1.

An example of a lead 1 for an active implantable medical device 99 is illustrated in FIGS. 1 and 2. The lead 1 includes an elongated, biocompatible, electrically non-conductive body 3. The elongated body 3 extends from a first portion 7 to a centre section 4 and finally to a second portion 9.

A plurality of electrical connectors 6 are at the first portion 7 near a proximal end whereby the connectors 6 are used to electrically connect to the active implantable medical device 99. A plurality of electrodes 8 are at the second portion 9 near a distal end of the elongated body 3. The electrodes 8 deliver therapy to the patient.

A plurality of electrically conductive filaments 5 are located inside the elongated body 3 to connect the electrical connectors 6 to corresponding electrodes 8. Referring to the example in FIG. 1, the electrically conductive filaments can be located in lumens 15 in the elongated body 3.

At least one elongated decoy conductor 10 is also located inside the elongated body 3 to mutually couple with the electrically conductive filaments 5. In particular, the decoy conductor 10 is coupled electromagnetically with the electrically conductive filaments 5 in the radio frequency spectrum. In further examples, this may be directed specifically at radio frequencies that correspond to those expected during MRI.

The at least one electrical conductor 10 has a higher electrical resistance than the plurality of electrically conductive filaments 5. This electrical resistance helps to dissipate energy from currents induced by radio frequencies during MRI.

In some examples, the decoy conductor 10 and electrically conductive filament 5 are mutually coupled similar to how radio antennas experience mutual coupling with a nearby antenna. That is, energy at the electrically conductive filament 5 can be transmitted, electromagnetically, by the nearby decoy conductor 10. In turn, the relatively higher resistance of the decoy conductor 10 causes the induced currents to be dissipated as heat. Since the decoy conductor 10 is located inside the elongated body 3, thermal conduction of this heat to surrounding tissue can be thermally insulated and/or reduced. This is in contrast to heating of the electrically conductive filaments 5 whereby heat can be thermally conducted to the electrodes 8, which in turn are in direct contact with tissue (and thereby cause tissue damage. Although mutually coupling can cause transfer in either direction (i.e. also from the electrically conductive filament 5 to the decoy conductor 10), the net energy transfer of some examples with the decoy conductor 10 results in less heat generated at the electrically conductive filament 5.

In some examples, the decoy conductor 10 also reduces the radio frequency (RF) energy near the electrically conductive filaments 5 to reduce heating issues at the electrically conductive filaments 5. In some examples, this includes the decoy conductor 10 having a conductor length ($L_1$) that is matched to absorb RF energy from expected wavelengths produced by an MRI. That is, the decoy conductor reduces the intensity of the electromagnetic fields that would otherwise be exposed to the electrically conductive filaments 5.

Details of various examples of the present disclosure will now be described.

The First Portion 7

The first portion 7, including the plurality of connectors 6, are configured to be inserted into the AIMD 99, whereby the connectors 6 are in electrical connection with respective connectors inside the AIMD. In one example, the connectors 6 are configured to be received in medical grade connector/contact systems such as those under the trade name "Bal Conn" offered by "Bal Seal Engineering". The connectors 6 are substantially annular (i.e. ring-shaped) and typically constructed of a biocompatible and electrically conductive material. The annular construction permits good electrical contact with the receiving contact in the AIMD. Suitable material for the connectors 6 may include, but is not limited to, platinum, iridium, and/or alloys thereof. In other examples, the connectors 6 can include a core of high conductance material such as cobalt, chromium, molybdenum or alloys thereof with a coating of metals such as platinum, tantalum, niobium, titanium or alloys thereof.

The connectors 6 are located separately along the first portion 7. In FIGS. 2 and 3b, this includes three connectors 6 spaced along the first portion 7 for illustrative purposes. However, it is to be appreciated that additional connectors 6, for additional channels, can be used. In some examples, this can include up to a dozen or more channels (with a corresponding dozen connectors 6, electrically conductive filaments 5, and electrodes 8). The whole length of the first portion 7 is typically inserted into the AIMD.

In addition to the connectors 6, the first portion 7 includes non-conductive part(s) that support the connectors 6. In some examples, this includes the same material, and can be part of, the elongated, biocompatible, electrically non-conductive body 3.

The Second Portion 9

The second portion 9 includes a plurality of electrodes 8 to deliver therapy to the patient. In some examples, the number of electrodes 8 are the same as the number of corresponding connectors 6, and in turn, the same number of electrically conductive filaments 5 that form the electrical connection.

The size and spacing of the electrodes 8 is selected based on the anticipated therapy to the patient. Typically, each electrode 8 has a longer axial length than the corresponding connector 6.

The non-conductive part(s) of the second portion 9 can be integrally formed with the body 3 of the centre section 4 and the first portion 7. Similarly, the electrically conductive filaments 5 are integrally formed and extend from the centre section 4 into the second portion 7.

Example of the Centre Section 4 of the Body 3 with Multiple Lumens 15

FIG. 1 is an example of a cross-section through the body 3 at the centre section 4, whereby the multiple outer lumens 15 are configured as a set of planetary lumens 15 around a core 35. The core 35 can include a central lumen 35 to accept a stylet to assist in insertion and implantation of the lead 1, after which the stylet is withdrawn.

The centre section 4 is typically the longest portion of the elongated body 4. The centre section 4 encloses the electrically conductive filaments 5 to minimise conduction between the electrically conductive filaments 5 to tissue immediately surrounding the centre section 4.

Furthermore, the centre section 4 enclose the at least one decoy conductor 10 to minimise thermal conduction between the decoy conductor 10 and the surrounding tissue.

The electrically conductive filaments 5 are located in a subset of the multiple lumens 15 that are separate from other lumens 15 that receive the decoy conductor(s) 10. Thus portions of the electrically non-conductive body 3 (i.e. walls between adjacent lumens 15) physically separates the electrically conductive filaments 5 from the decoy conductor 10 to avoid electrical conduction with one another. The decoy conductor(s) 10 are also electrically insulated from the connectors 6 and the electrodes 8.

In the example of FIG. 1, the multiple lumens 15 include a dozen lumens, with eight lumens occupied by eight respective electrically conductive filaments 5 and four lumens occupied by four respective decoy conductors 10. The eight electrically conductive filaments 5 provide eight channels for therapeutic use. The four respective decoy conductors 10 are equally spaced apart to assist in evenly dissipating energy induced by the RF fields.

In some examples, each electrically conductive filament 5 has a decoy conductor 10 in at least one adjacent lumen 15. Such a configuration provides a decoy conductor 10 close to the electrically conductive filament 5 that can assist in more effective dissipation of unwanted energy that can damage tissue during an MRI.

It is to be appreciated that other numbers and configurations of lumens 15 can be used. In another example, a four channel system may include six lumens 15. This can include a first and second lumen 15 for two electrically conductive filaments 5, followed by a third lumen 15 for an elongated decoy conductor 10, followed by fourth and fifth lumens 15 for another two electrically conductive filaments, and a sixth lumen 15 for another elongated decoy conductor 10. The lumens 15 are configured in a loops such that the first and sixth lumen 15 are adjacent one another so that the other elongated decoy conductor 10 is adjacent the electrically conductive filament 5 in the first lumen. Additional configurations can include two, three, five, six, seven, nine, or more channels with additional lumens to accommodate the decoy conductor 10.

The body 3 is made of biocompatible, electrically non-conductive material that can include thermoplastic polyurethanes (TPUs) such as those under the trade name "pellethane" offered by "The Lubrizol Corporation". In some examples, the body 3 is made from an extrusion of a flexible material to create multiple lumens 15 therein. In some examples, the body 3 and the electrically conductive filaments 5 are mated together with a drawn filled tubing process. In yet further examples, the elongated decoy conductor(s) are also mated to the body 3 using the drawn filled tubing process. The lead 1 is constructed to allow a degree of flexibility to allow placement and conformity with the patient's anatomy.

The electrically conductive filaments 5 is preferably selected from a configuration of biocompatible materials. This can include single core or multi strand wires. In another example, this can include a composite of a medical grade alloy, with the trade name "35N LT" offered by Fort Wayne Metals, having a silver core. In another specific example, the conductive filaments 5 include a wire jacket of 35N LT (Nickel-Cobalt-Chromium alloy) per ASTM F562 and of a composition which includes <0.01 wt % titanium, and a wire core of silver 28% of the cross-sectional area of the electrically conductive filament 5.

The lead 1 are constructed and/or selected to a length suitable for the therapy and patient's characteristics. In some examples, the lead 1 is in the range of 600 mm to 900 mm in length. In yet other examples, the lead 1 is in the range of 500 mm to 1200 mm in length.

The Elongated Decoy Conductor 10

An example of the elongated decoy conductor 10 will now be described with reference to FIGS. 3a and 3b. For clarity, this simplified example only illustrates two electrically conductive filaments 5 and one elongated decoy conductor 10, but it should be appreciated that these principles can, where practical, be applied to other leads 1 with additional channels.

Figure 3A:
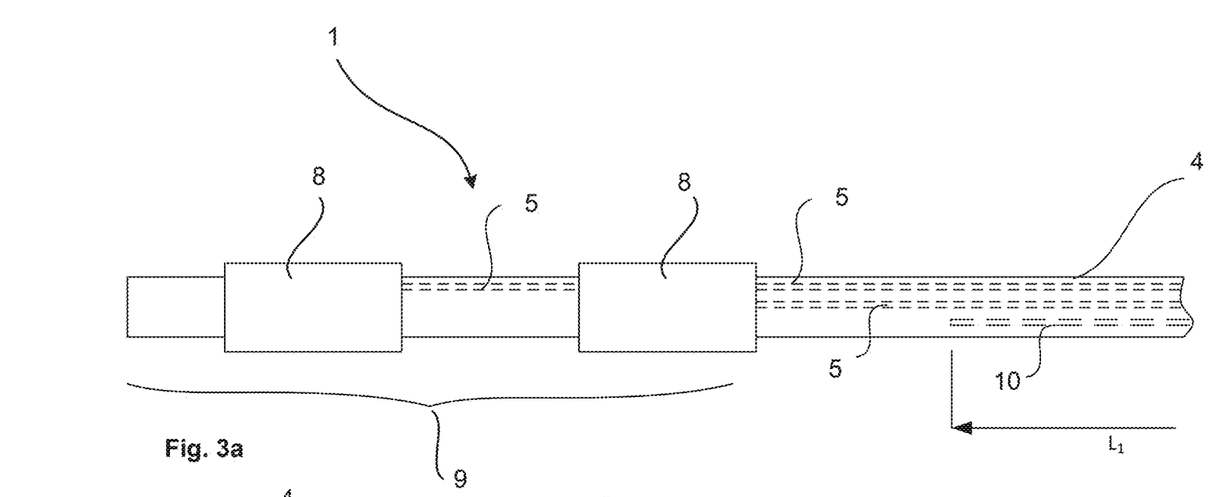
FIG. 3a shows a distal end with electrodes and FIG. 3b shows a proximal end with connectors.
Figure 3B:
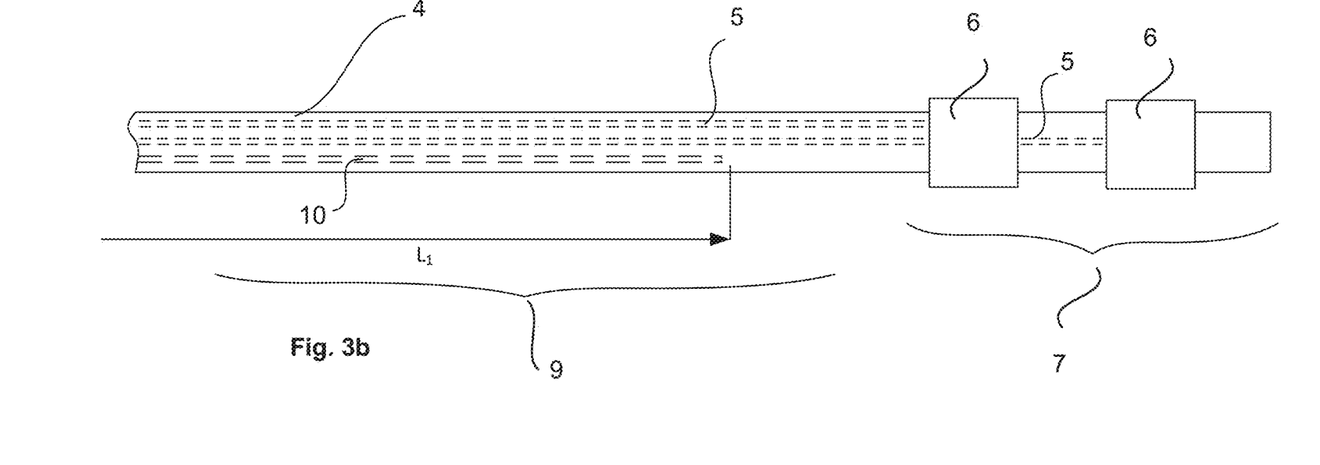
Figures 4A, 4B:
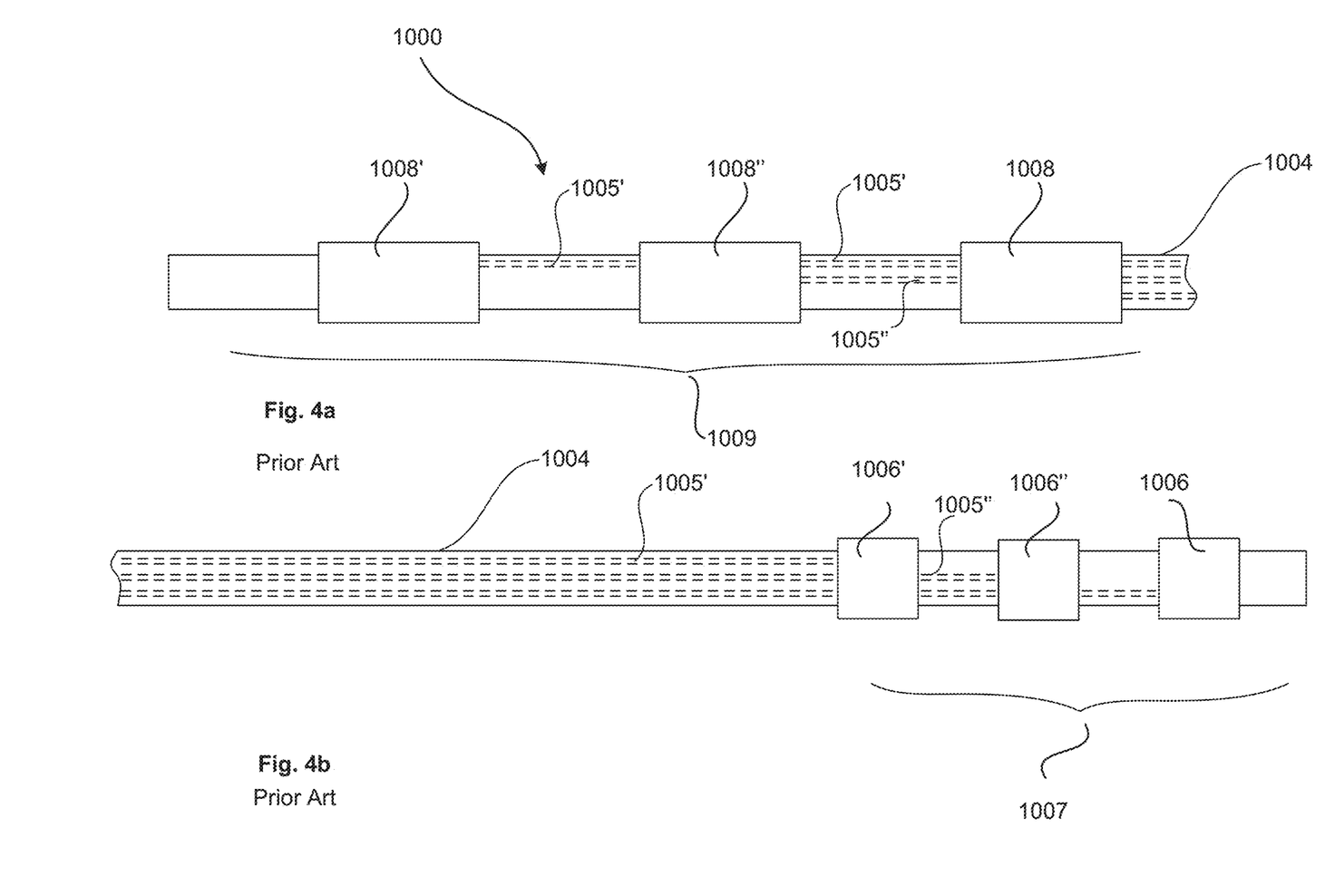
FIGS. 4a and 4b illustrate an example of a prior art lead.
Figure 5:
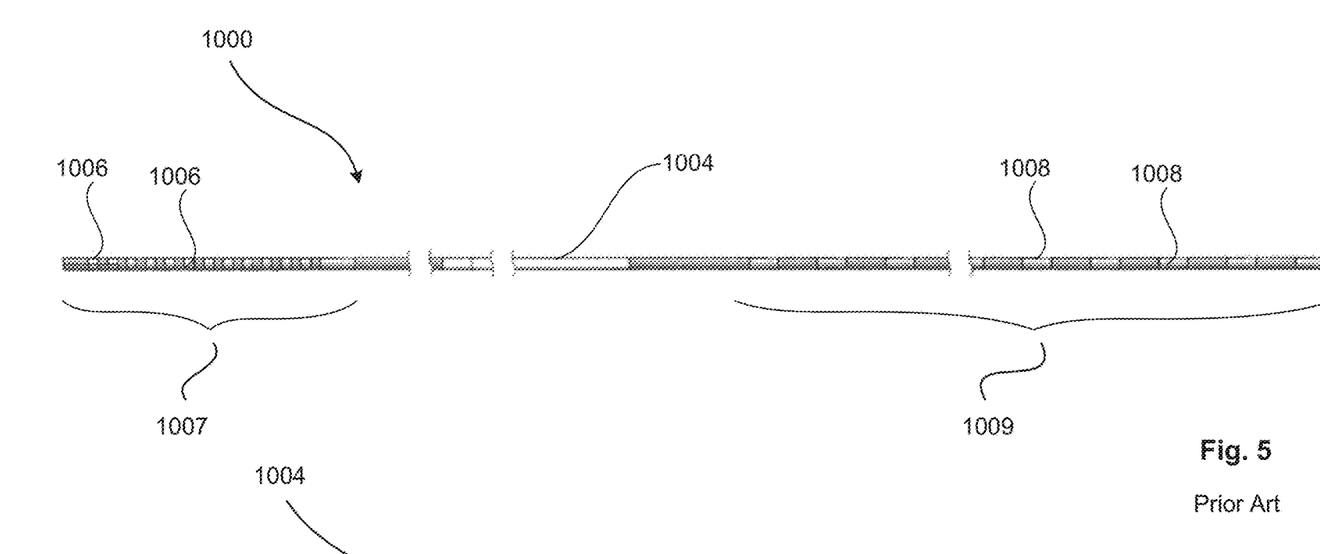
FIGS. 5 illustrates another view of a prior art lead.
Figure 6:
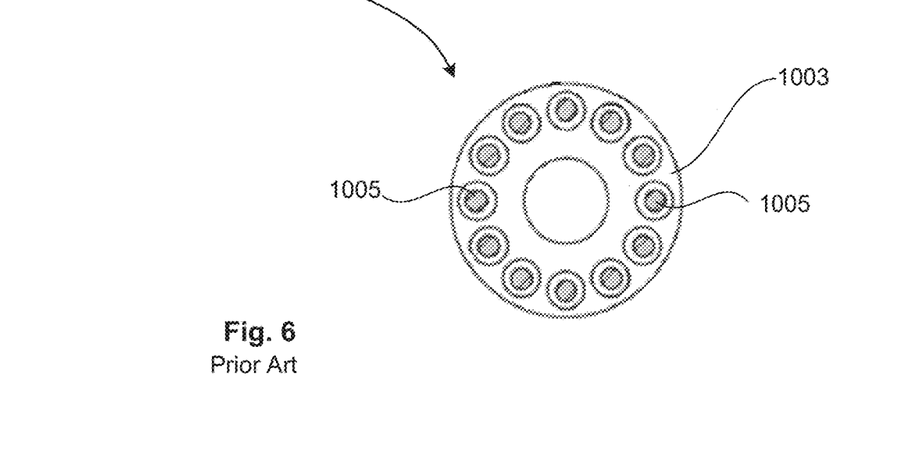
FIG. 6 illustrates a cross section of the prior art lead in FIG. 5.

The elongated decoy conductor 10 can be located substantially parallel to the plurality of electrically conductive filaments 5 as shown in FIGS. 3a and 3b. In some examples, configuring the elongated decoy conductor 10 parallel to adjacent electrically conductive filaments 5 can enhance the mutual coupling.

The elongated decoy conductor 10 has a conductor length $L_1$ that is shorter than each of the plurality of electrically conductive filaments 5.

In some examples, the conductor length $L_1$ is in the range of 60% to 90% of the overall length of the lead 1. In some other examples, the conductor length $L_1$ is approximately 90% of the overall length of the lead 1.

In some examples, the conductor length $L_1$ is matched with an expected wavelength of an RF field from an MRI. MRI can operate with RF fields in the 50 to 250 MHz range. In some specific examples, this can include scanning at approximately 64 MHz. In other examples, this can include scanning at approximately 128 MHz.

In some examples, matching the conductor length $L_1$ includes selecting a length that is an integer multiple of half the expected wavelength from the MRI. In some specific examples, this includes selecting an odd integer multiple of the expected half wavelength from the MRI.

In yet another example, matching the conductor length $L_1$ includes selecting a length that is equal to the expected wavelength from the MRI.

Although one approach is to select a conductor length $L_1$ appropriate to the expected wavelength from the MRI, it is to be appreciated that the converse can also apply. That is, a lead 1 with a particular conductor length $L_1$ is implanted in a patient. The particular conductor length $L_1$ is recorded and from there, one or more "safe" operating frequencies for MRI can be determined for that patient.

In some examples, the conductor length $L_1$ is in the range of 500 mm to 900 mm.

In some examples, each of (or the) elongated decoy conductor 10 has a diameter in the range of 70 µm to 200 µm.

The resistance of the elongated decoy conductor 10 is higher than the electrically conductive filaments so that energy is taken from adjacent filaments 5 dissipated at the decoy conductor 10. In some examples the elongated decoy conductor 10 has a total resistance in the range of 300 to 1000 ohms per metre. In some examples, the resistivity of the decoy conductor 10 can be used (or selected) to enhance the electromagnetic coupling with the electrically conductive filaments 5.

In some examples, the elongated decoy conductor 10 is made of nichrome (an alloy of nickel and chromium, and in some other examples, additional elements). In other examples, the elongated decoy conductor 10 is made of carbon fibre. It is to be appreciated that other resistive conducting material can be used. Preferably, the material is biocompatible even though the material is inside a biocompatible body 3. Furthermore, the material should have a degree of flexibility to allow flexing with the other parts of the flexible lead 1.

Specific Examples of the Elongated Decoy Conductor

In some examples, the planetary lumens 15 in the lead 1 each have a diameter of 220 µm. Such sized lumens 15 can receive 42 gauge nichrome wire specified with an approximate impedance of 228 ohms per metre and with a diameter of 78 µm. In some examples, this can include use with the twelve lumen 15 and four elongated decoy conductor 10 configuration illustrated in FIG. 1.

In another example, a carbon fibre wire with a diameter of 200 µm and an impedance of 1000 ohms per metre.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A lead for an active implantable medical device comprising:
    an elongated, biocompatible, electrically non-conductive body;
    a plurality of electrically conductive filaments inside the elongated body to electrically connect electrical connectors to corresponding electrodes; and
    at least one elongated decoy conductor inside the elongated body to electromagnetically couple with the plurality of electrically conductive filaments,
    wherein the at least one elongated decoy conductor has a higher electrical resistance than the plurality of electrical conductive filaments to dissipate energy from currents induced by radio frequencies, and wherein the elongated body includes multiple lumens, wherein the electrically conductive filaments are located in a subset of the multiple lumens that are separate from other lumens, in the multiple lumens, that receive the at least one elongated decoy conductor.

2. A lead according to claim 1, wherein the at least one elongated decoy conductor is located substantially parallel to the plurality of electrically conductive filaments.

3. A lead according to claim 1, wherein the at least one elongated decoy conductor is electrically insulated from the plurality of electrically conductive filaments, connectors and electrodes by the elongated body.

4. A lead according to claim 1, wherein the multiple lumens are arranged as a set of planetary lumens around a core of the elongated body.

5. A lead according to claim 1, wherein the multiple lumens include a dozen lumens.

6. A lead according to claims 1, wherein the at least one elongated decoy conductor includes two or more elongated decoy conductors evenly spaced from each other in the multiple lumens.

7. A lead according to claim 1, wherein the at least one elongated decoy conductor includes four elongated decoy conductors evenly spaced from each other in the multiple lumens.

8. A lead according to claim 1, wherein the at least one elongated decoy conductor is shorter than each of the plurality of electrically conductive filaments.

9. A lead according to claim 1, wherein a conductor length of the at least one elongated decoy conductor is approximately 90% of a length of the lead.

10. A lead according to claim 1, wherein a conductor length of the at least one elongated decoy conductor is matched with an expected wavelength of a radio frequency (RF) field from an MRI.

11. A lead according to claim 10, wherein a conductor length includes odd integer multiples of half the expected wavelength of the RF field from the MRI.

12. A lead according to claim 1, wherein a conductor length of the at least one elongated decoy conductor is in the range of 500 mm to 900 mm.

13. A lead according to claim 1, wherein a conductor length of the at least one elongated decoy conductor is in the range of 10% to 90% of the length of the longest electrically conductive filament.

14. A lead according to claim 1, wherein the at least one elongated decoy conductor has a length specific resistance of 300 to 1000 Ohms/metre.

15. A lead according to claim 1, wherein the at least one elongated decoy conductor comprises: nichrome and/or carbon fibre.

16. A lead according to claim 1, wherein each of the at least one elongated decoy conductors has a diameter of 70 µm to 200 µm.

17. A lead according to claim 1, wherein the elongated, biocompatible, electrically non-conductive body comprises thermoplastic polyurethane.

\* \* \* \* \*